Figure 1:
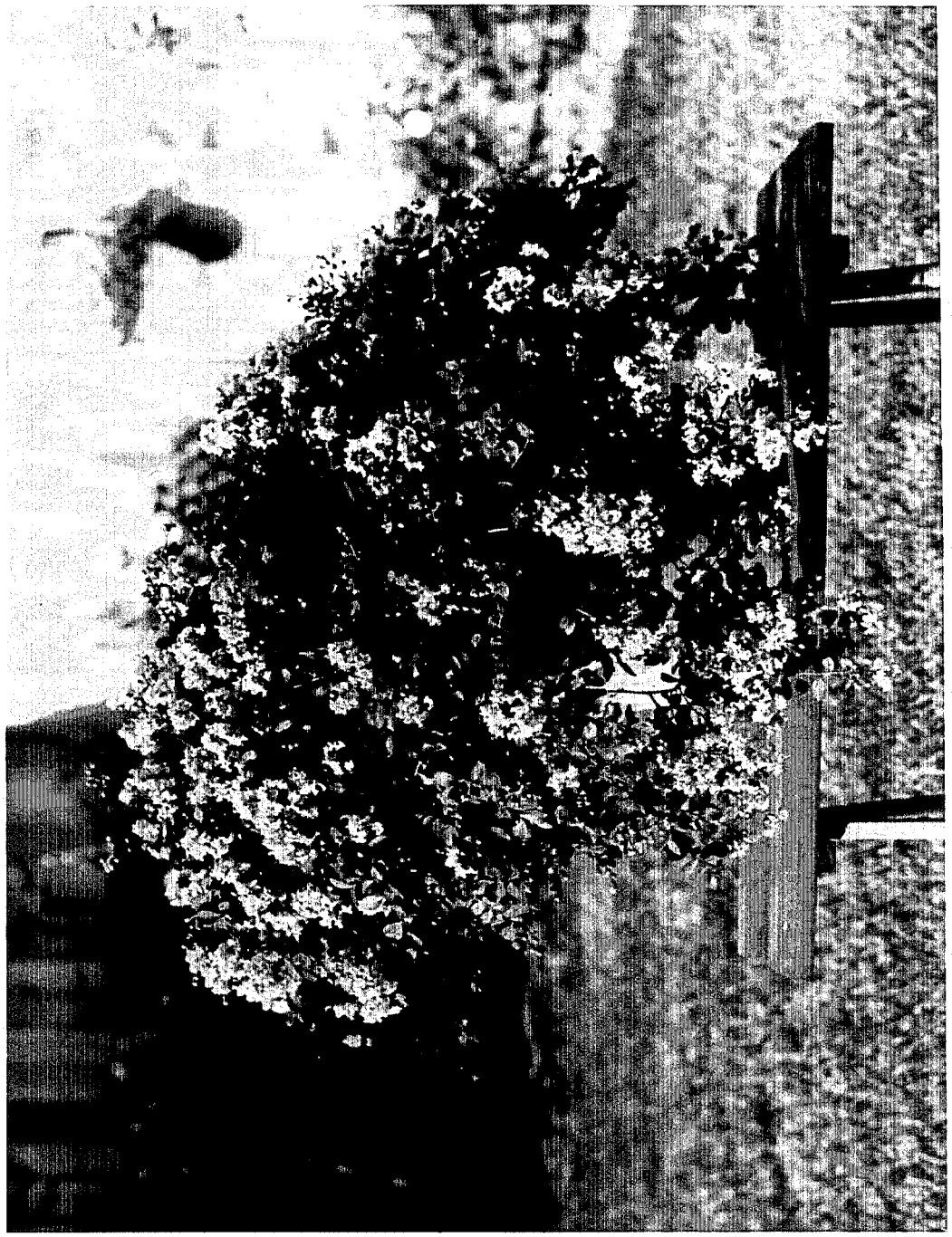

United States Patent [19]

Chopin

[11] Patent Number: Plant 5,284

[45] Date of Patent: Sep. 18, 1984

[54] CREPE MYRTLE

[75] Inventor: David E. Chopin, Baton Rouge, La.

[73] Assignee: Chopin & Wright, Baton Rouge, La.

[21] Appl. No.: 354,950

[22] Filed: Mar. 5, 1982

[51] Int. Cl.[3] ..... A01H 5/00
[52] U.S. Cl. ..... Plt./54
[58] Field of Search ..... Plt./54

*Primary Examiner*—Robert E. Bagwill
*Attorney, Agent, or Firm*—Thomas E. Balhoff

[57] ABSTRACT

A new and distinct variety of the *Lagerstroemia indica* characterized as to novelty by a dwarfness in size, lack of continual vertical growth after maturity and a weeping growth habit at full maturity.

1 Drawing Figure

1

The present invention relates to a new and distinct variety or ornamental shrub of the species *Lagerstroemia indica,* commonly known as crepe myrtle, characterized as to novelty by its height of 12–24 inches or less at full maturity with substantially no vertical growth thereafter as described in the following paragraphs and illustrated in the accompanying color photograph. The new variety has been developed by me during the past five years by crossing unnumbered or unnamed seedlings to produce a new ornamental plant which will grow to a height of no more than 12–24 inches at maturity.

Compact crepe myrtles have been asexually reproduced by others but such plants have been characterized by a continual annual growth after maturity of from 6–8 inches. See U.S. Plant Pat. No. 2,551. Thus, even though these plants are described as dwarf or compact, after several years growth, they will have attained a height far in excess of applicant's plant. The present plant reaches its mature height of 12–24 inches or less and does not continue to grow vertically as the plants of the prior art.

The plant has been asexually reproduced at Baton Rouge, La., by means of hardwood and softwood cuttings. All descendants have shown the same characteristics as the original plant, indicating that the new variety is thereby well established. The plant does not produce true from seed.

The plant of the new variety is resistant to freezing and has demonstrated good winter hardiness. The plant has survived temperatures as low as 10° F.

The new variety does not resemble in size or growth habit the original parent plants from which it was derived.

A plant of the new variety is shown in full color in the accompanying photograph. A detailed description of the new variety follows, and to facilitate identification of the important colors, the terminology adapted by The R.H.S. Colour Chart has been followed.

2

THE PLANT

Parentage: The pollen and seed parents of this plant were unnumbered or unnamed seedlings that had shown desirable characteristics of dwarfness, resulting from previous crosses made by me. The seeds are fertile.

Growth: The plant is comparatively compact, weeping, with its width typically exceeding its height. At maturity, the plant will reach a maximum height of 12–24 inches and will grow 6 to 10 inches in height during the first year. There is substantially no vertical growth subsequent to reaching full maturity.

Branches: Multiple branches are freely produced by young cuttings. The branches grow horizontal rather than vertical and are red when immature, turning brown upon maturity. The mature width is 36–42 inches.

Foliage: The leaf arrangement is best described as alternate and are grouped by twos on opposite sides of the stem when mature with a simple type of leaf having an elliptic to ovate shape. Generally, the leaf will have an acute tip, obtuse base, and entire margin. The leaf attachment is stalked, and the leaf venation is pinnate. The leaves will grow in length to 4–5 centimeters and in width to 2–4 centimeters. Finally, the leaf will be No. 147A (Woodpecker Green) color.

Flower: The complete flowers will be 2–3 centimeters high and have a width of 2–4 centimeters, and the flower clusters appear as terminal panicles. There are three to eight florets per flower cluster. The bloom period is July to October.

Color: The color of the blossom is No. 80C.

I claim:

1. A new distinct variety of *Lagerstroemia indica* plant substantially as shown and described, characterized by the distinctive purple color, its height up to 12–24 inches, substantially no vertical growth at full maturity, and a weeping growth habit at full maturity.

* * * * *